July 29, 1958 E. V. GOLDSMITH ET AL Plant Pat. 1,737
VARIETY OF STRAWBERRY
Filed June 29, 1956
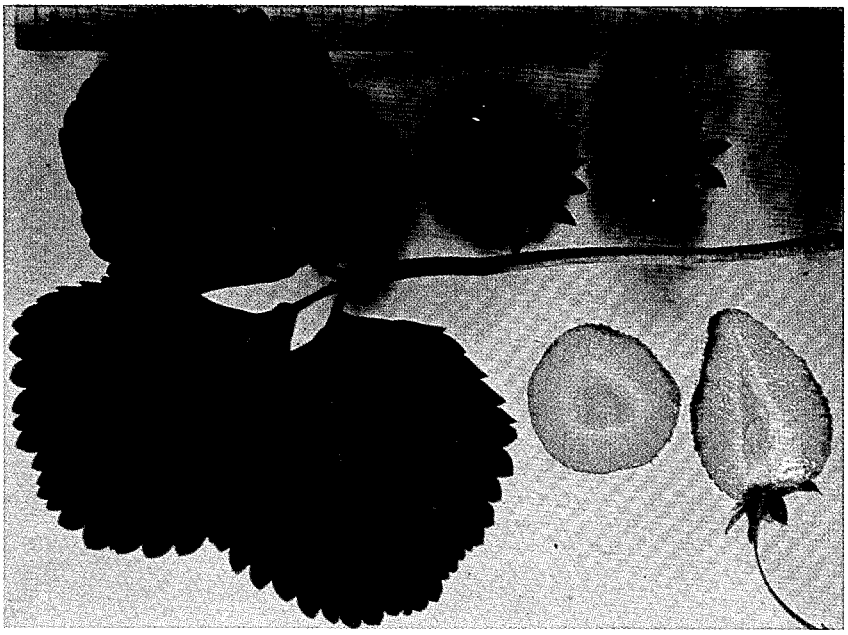
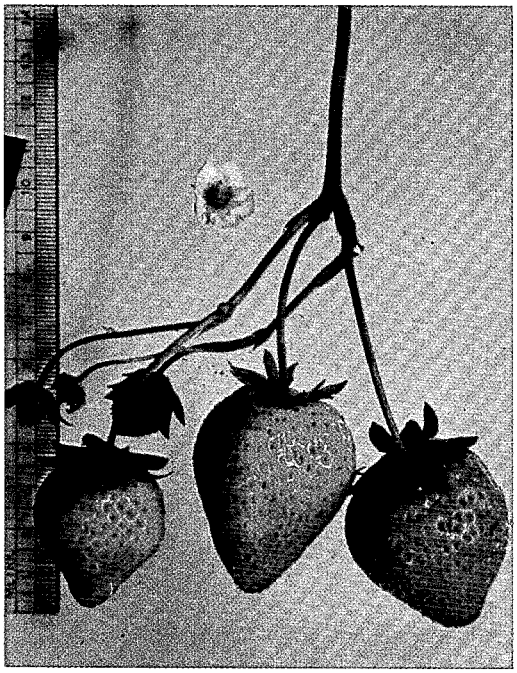
INVENTORS
HAROLD E. THOMAS and
MARGARET S. GOLDSMITH
EXECUTRIX FOR THE ESTATE OF
EARL V. GOLDSMITH
BY Hansen and Lane
THEIR ATTORNEYS United States Patent Office Plant Pat. 1,737
Patented July 29, 1958

1,737

VARIETY OF STRAWBERRY

Earl V. Goldsmith, deceased, late of Morgan Hill, Calif., by Margaret S. Goldsmith, executrix, San Jose, and Harold E. Thomas, Morgan Hill, Calif.; said Margaret S. Goldsmith assignor to The Strawberry Institute of California Application June 29, 1956, Serial No. 595,040

1 Claim. (Cl. 47—62)

This invention relates to a distinctly new strawberry variety resulting from a cross of two University of California seedling selections numbered 638.45 and 794.19. Seedlings resulting from this cross were first fruited at Waterford, California, and the plant of this invention was selected from this group of seedlings and further asexual reproduction was carried out in the same area by rooting runner plants which originated from the mother seedlings. Further testing carried on in various parts of California during the intervening seasons proved this selection to have merit in numerous locations on properties of members of The Strawberry Institute of California In the accompanying drawing two photographic pictures are presented:

The uppermost picture shows a view of one leaf of the plant showing the color and characteristics thereof; the calyx bud of the fruit; the fruit side view of the calyx from which the fruit has been removed; a transverse section through the fruit; and a longitudinal section through the fruit and calyx.

The lowermost picture shows a side view of an inflorescence or blossom and also a fruit bearing stem.

The plant embodying the present invention is slow to start in the spring in fruiting beds, but later grows rapidly and eventually becomes a large, semi-open crowned, vigorously growing plant. It is very susceptible to spider mites which at times are responsible for retarding spring growth. The foliage is upright, robust, stiff and is taller than that of the Shasta variety. The Shasta is a variety introduced in 1945 by applicants herein for the University of California. The Shasta is a standard variety grown in California more than in any other State. The Shasta variety although not patented is known to the Bureau of Plant Industry Agricultural Research Center at Beltsville, Maryland. The foliage color in the plant of the present application is much lighter green than in the Shasta variety in that it gives a somewhat yellow cast to the field. In the nursery the plant is a very good runner maker.

The fruit of the present plant is more conic than that of the Shasta variety and is normally larger and lighter in color in comparison thereto. In the plant of the present invention the berries are borne on long inflorescences with the pedicel of the primary berry and secondary fruiting stems branching from a common axil high upon the main fruiting stem as illustrated in Fig. 6. The hair on the pedicel of the present plant may make an angle with the pedicel equal to that which occurs in the Shasta variety, but it is often of smaller degree. In contrast to the calyx in the Shasta variety, the calyx of the fruit in the present plant is smaller, lighter in color and not serrated. The berry of this new plant with its bright glossy appearance and large size makes a superior packaged product, and holds this characteristic reasonably well on interstate shipment as well as in local markets. The moderately red flesh of the berries of this new plant gives an acceptable color to the sliced frozen fruit and with other desired qualities it is rated as a good berry for freezing purposes.

The fruiting season for this new variety is normally about the same as for the Shasta variety except that it is somewhat more continuous during the summer. It usually starts bearing between the 15th and 20th of April, reaching a peak in production around the 15th or 20th of May in the interior and warmer coastal valleys of California, and with ups and down in production it bears until cold weather or fall rains occur. In southern California production on this new plant starts much earlier in the year and in cool coastal areas somewhat later. When plants of this new variety are set out in late fall or early winter in the southern or coastal areas tests have shown that a good crop can often be harvested the first year. In this respect it is contemplated that this new variety will usually bear much heavier than does the Shasta variety.

A defect often shows in the fruit of the present plant during summer crop wherein the tips of the primary and secondary berries have a tendency to become furrowed and seedy. In this connection white tips sometimes occur and nubbins or button berries can also be found.

In comparison to the fruit of the Shasta variety, the dessert quality of the berries of this new variety is about equal and has a mild sub-acid flavor. The berry of this new plant has no particular aroma. The fruit of this invention is somewhat firmer than that of the Shasta variety and the skin is slightly tougher. The seeds on these new berries are even with the surface thereof or slightly exerted, medium in size and medium in spacing.

This new variety of plant is susceptible to Verticillium wilt; the red stele disease; two spotted mite and cylamen mite. Both fruit and foliage of this new plant is moderately affected by mildew.

The detailed varietal characteristics described below were observed in second year test beds during August, September and October at Watsonville, California, which is a cool coastal area near the ocean. The color terminology is in accordance with Ridgeways Color Standards and Nomenclature (1912 edition).

Plant: Tall, vigorous, semi-open, with a vigorous root system and good longevity.

Leaves: Petiole-long, mostly between 15 and 25 cm.; petiolule of central leaflet 5 to 10 mm. long with an average of 8 mm. Color—Cosse Green, Plate V. Leaflet—large with diameter of central leaflet 6.5 to 9 mm. Main vein on upperside of central leaflet of vigorous leaves is noticeably wide, 1 to 2 mm. at union with petiolule and extends outward 10 mm. Leaflets have a slightly rugose or wrinkled surface with a wavy contour and are held on an erect petiole. The outline of the serrations on the margins of the leaflets is ovate with an acute apex. Color—upperside—Spinach Green, Plate V; lowerside, Light Bryce Green, Plate XVII.

Runners: Vigorous, long internodes, many runners and runner plants produced the first year and a few the second on fruiting beds. The nursery production of runner plants is medium high.

Inflorescence: Long, mostly 20 to 30 cm. Most of the inflorescences have the pedicel of the primary fruit and the peduncle of the secondary fruit originating from a central axil on the main fruiting stem or main peduncle. Most hair on the tertiary pedicels 20 mm. below the flowers lays against and parallel with the pedicels. Some hair may be held irregularly between an angle of 10 to 35 degrees with the pedicel. Flowers of the inflorescence are partially visible above the foliage.

Fruit: Large, 35 to 40 mm. wide, and 40 to 50 mm. long (size of primaries or well developed secondaries); long conical and uniformly symmetrical with tapering rounded shoulders. The fruit of the summer crop may develop seedy tips or seedy folds at or near the apex. The apex may remain whitish green on ripe berries during summer crops and there is often a whitish neck produced during these crops. The surface is glossy and bright. Color—varies between Spectrum and Carmine Red, Plate I. Seeds—medium size, held even to slightly above the surface; uniformly spaced except where a few non-fertile seeds are produced causing the seedy folds and tips mentioned above. Seed color—Apricot Yellow, Plate IV. Flesh—juicy, firm. Color—Scarlet Red, Plate I. The skin is reasonably firm.

Calyx: Comparatively small, 23 to 33 mm. in diameter and averaging 29 mm. and pale in color. Tends to be free of the fruit giving a reflexed appearance. Sepals—mostly 10 to 15 in number, producing an acute apex which is not serrated. Two rows of sepals are produced which overlap slightly, the row nearest the fruit producing sepals which are wide at their base and the row fartherest from the fruit having sepals that narrow down at their base to give a lanceolate outline. Color—upperside (next to fruit)—Chromium Green, Plate XXXII; lowerside—Chrysolite Green, Plate XXXI.

We claim:

A new and distinct variety of strawberry plant, substantially as herein shown and described, characterized by a large vigorous plant which bears long conical, glossy fruit having excellent shipping and processing qualities; and by its capacity to fruit well the first year in cool areas and its ability to produce a high yield during a long fruiting season.

No references cited.